United States Patent
Burt et al.

(10) Patent No.: US 9,198,852 B2
(45) Date of Patent: Dec. 1, 2015

(54) PERSONAL CARE COMPOSITIONS COMPRISING SQUASH OR PUMPKIN EXTRACT

(75) Inventors: Johnny Burt, Dawsonville, GA (US); Kathy Burt, Dawsonville, GA (US); Tyler Goodwin, Dawsonville, GA (US)

(73) Assignee: BURT'S FARM, LLC, Dawsonville, GA (US)

( * ) Notice: Subject to any disclaimer, the term of this patent is extended or adjusted under 35 U.S.C. 154(b) by 216 days.

(21) Appl. No.: 13/596,645

(22) Filed: Aug. 28, 2012

(65) Prior Publication Data

US 2013/0058885 A1    Mar. 7, 2013

Related U.S. Application Data

(60) Provisional application No. 61/530,667, filed on Sep. 2, 2011.

(51) Int. Cl.
| | | |
|---|---|---|
| A61K 36/42 | (2006.01) | |
| A61K 8/97 | (2006.01) | |
| A61Q 5/02 | (2006.01) | |
| A61Q 5/12 | (2006.01) | |
| A61Q 19/00 | (2006.01) | |
| A61Q 19/10 | (2006.01) | |

(52) U.S. Cl.
CPC ... *A61K 8/97* (2013.01); *A61Q 5/02* (2013.01); *A61Q 5/12* (2013.01); *A61Q 19/00* (2013.01); *A61Q 19/10* (2013.01)

(58) Field of Classification Search
USPC .......................................................... 424/758
IPC ..................................................... A61K 36/43
See application file for complete search history.

(56) References Cited

U.S. PATENT DOCUMENTS

| | | | |
|---|---|---|---|
| 5,124,313 A | | 6/1992 | Schaeffer et al. |
| 5,194,253 A | * | 3/1993 | Garrido ...................... 424/78.03 |
| 5,468,511 A | | 11/1995 | Zeidler |
| 5,543,146 A | | 8/1996 | Perez |
| 5,547,673 A | * | 8/1996 | Bombardelli ................. 424/758 |
| 5,653,997 A | * | 8/1997 | Renimel et al. ............... 424/450 |
| 5,976,548 A | | 11/1999 | Hsia et al. |
| 6,045,779 A | | 4/2000 | Mueller et al. |
| 6,117,429 A | | 9/2000 | Bucci |
| 6,146,645 A | | 11/2000 | Deckers et al. |
| 6,187,811 B1 | | 2/2001 | Lane |
| 6,197,309 B1 | | 3/2001 | Wheeler |
| 6,200,594 B1 | | 3/2001 | Ernest et al. |
| 6,241,987 B1 | | 6/2001 | Lam |
| 6,261,607 B1 | | 7/2001 | Newmark et al. |
| 6,270,774 B1 | | 8/2001 | Hsia et al. |
| 6,372,234 B1 | | 4/2002 | Deckers et al. |
| 6,582,710 B2 | | 6/2003 | Deckers et al. |
| 6,596,266 B2 | | 7/2003 | Catalfo et al. |
| 6,599,513 B2 | | 7/2003 | Deckers et al. |
| 6,607,755 B2 | | 8/2003 | Farley |
| 6,649,781 B2 | | 11/2003 | Tou |
| 6,869,621 B2 | | 3/2005 | Hwang et al. |
| 6,896,910 B2 | | 5/2005 | Kim et al. |
| 7,122,213 B2 | | 10/2006 | Anno et al. |
| 7,166,300 B1 | | 1/2007 | Dascalu |
| 7,192,731 B2 | | 3/2007 | Kanner et al. |
| 7,306,808 B2 | | 12/2007 | Ching et al. |
| 7,371,389 B2 | | 5/2008 | Keefe et al. |
| 7,479,292 B2 | | 1/2009 | Robinson |
| 7,547,211 B2 | * | 6/2009 | Swanick ......................... 434/84 |
| 7,629,005 B2 | | 12/2009 | Popp |
| 7,741,500 B2 | | 6/2010 | Arhancet et al. |
| 7,815,960 B2 | | 10/2010 | Quan et al. |
| 7,867,525 B2 | | 1/2011 | Bok et al. |
| 8,003,086 B2 | | 8/2011 | Chodorowski-Kimmes |
| 8,062,688 B2 | | 11/2011 | Greither |
| 8,221,746 B2 | | 7/2012 | Isaacs et al. |
| 2007/0110833 A1 | * | 5/2007 | Jin et al. ......................... 424/758 |
| 2007/0166253 A1 | | 7/2007 | Kostick et al. |
| 2007/0196298 A1 | | 8/2007 | Kostick et al. |
| 2008/0038388 A1 | * | 2/2008 | Paufique ....................... 424/758 |
| 2008/0089906 A1 | * | 4/2008 | Rival et al. .............. 424/195.17 |
| 2009/0226384 A1 | * | 9/2009 | Mukhopadhyay et al. ..... 424/49 |
| 2009/0269375 A1 | * | 10/2009 | Patnode ......................... 424/401 |
| 2010/0015073 A1 | | 1/2010 | Clavel et al. |
| 2011/0142775 A1 | | 6/2011 | Kostick et al. |

(Continued)

FOREIGN PATENT DOCUMENTS

| | | | |
|---|---|---|---|
| CN | 1389238 | | 1/2003 |
| DE | 4241893 | | 6/1993 |
| JP | 2008088105 | | 4/2008 |
| JP | 2009167119 | | 7/2009 |
| KR | 2003/005463 | * | 1/2003 |
| KR | 2003/067928 | * | 8/2003 |
| KR | 2005/107372 | * | 11/2005 |
| KR | 2007/121239 | * | 12/2007 |
| KR | 2008/059818 | * | 7/2008 |
| RU | 2058133 | * | 4/1996 |

OTHER PUBLICATIONS

Arcona Pumpkin Lotion, available at www.amazon.com/ARCONA-Pumpkin-Lotion-10%25-Regenerate/dp/B000265EWI/ref=sr_1_23?s=bea, downloaded Sep. 4, 2012.
Incredible Pumpkin Peel, available at www.mychelle.com/Incredible-Pumpkin-Peel-1-oz, downloaded Aug. 15, 2012.
Mychelle.com Search Results, available at www.mychelle.com/Search?search=pumpkin; downloaded Aug. 15, 2012.
Nourishing Shampoo, available at www.yestocarrots.com/product/nourishing-shampoo?product_id=1221007, downloaded Sep. 4, 2012.
Pumpkin Extract, available at www.makingcosmetics.com/Pumpkin-Extract-p.991.html, downloaded Apr. 30, 2012.
Pumpkin Honey Glycolic Mask, available at http://andalou.com/index/php/pumpkin-glycolic-brightening-mask.html, downloaded Aug. 15, 2012.

(Continued)

*Primary Examiner* — Chris R Tate

(74) *Attorney, Agent, or Firm* — Kilpatrick Townsend & Stockton LLP

(57) ABSTRACT

Embodiments of the present invention relate to novel personal care compositions for cleaning and moisturizing the skin or hair comprising an extract of squash and/or pumpkin, a preservative and a cosmetic base. Other embodiments of the present invention relate to methods of making and methods of using the personal care compositions.

26 Claims, No Drawings

(56) References Cited

U.S. PATENT DOCUMENTS

2012/0121743 A1* 5/2012 Garnier et al. ............... 424/777
2013/0101530 A1* 4/2013 Koshti et al. ................ 424/59

OTHER PUBLICATIONS

Pumpkin Peel, available at www.amazon.com/MyChelle-Incredible-Pumpkin-Peel-1-2-Ounce/dp/B000MAOWOS/ref=sr_1_1?s=be; downloaded Sep. 4, 2012.

Pumpkin Renew Cream, available at www.mychelle.com/Pumpkin-Renew-Cream-1 oz., downloaded Aug. 15, 2012.

Yes to Carrots Nourishing Carrot Shampoo, available at www.amazon.com/Yes-To-Carrots-Nourishing=16-9-Ounce/dp/B001EWET8W, downloaded Sep. 4, 2012.

Yes to Daily Balancing Moisturizer, available at www.amazon.com/Yes-to-Balancing-Moisturizer-Tomatoes/dp?b003PL2D6A, downloaded Sep. 4, 2012.

International Patent Application PCT/US2012/052650, International Preliminary Report on Patentability mailed on Mar. 27, 2014, 9 pages.

Butterbeer, pumpkin juice & other Harry Potter inspired recipes, What's on Sanya, Food & Wine > WOS Cooking Recipes, Jul. 13, 2011, 2 pages.

Incredible Pumpkin Peel, retrieved from the Internet: URL:http://www.mychelle.com/Incredible-Pumpkin-Peel-1-oz, Jun. 2011, 16 pages.

Pumpkin Hydrating Mist, http://www.gnpd.com, MINTEL database accession No. 1142340, Jul. 2009, 7 pages.

Pumpkin Rehydrating Shampoo, http://www.gnpd.com, MINTEL database accession No. 575869, Aug. 2006, 2 pages.

International Patent Application No. PCT/US2012/052650, International Search Report and Written Opinion mailed Mar. 12, 2014, 12 pages.

Chinese Patent Application No. 201280054019.3, Office Action mailed Jun. 2, 2015, 18 pages. (6 pages for the original document and 12 pages for the English translation).

\* cited by examiner

PERSONAL CARE COMPOSITIONS COMPRISING SQUASH OR PUMPKIN EXTRACT

PRIOR RELATED APPLICATIONS

The present application claims the benefit of priority to U.S. Provisional Application No. 61/530,667 filed Sep. 2, 2011 which is incorporated herein by reference in its entirety.

FIELD OF THE INVENTION

The present invention relates to novel personal care compositions for cleaning and moisturizing the skin or hair comprising an extract of squash and/or pumpkin and methods of making and using them.

BACKGROUND

Personal care compositions such as shampoos, conditioners, body washes, face creams, and lotions, and methods of using them, are a normal part of daily life. Such personal care compositions are useful for nourishment and maintenance of the health of the skin and hair and improve the physical appearance of consumers. However, many personal care compositions are made from chemicals that consumers are unfamiliar with and that are derived from non-natural sources. There is rising interest in products that are made from natural sources that are effective, environmentally friendly and familiar to consumers. What is needed, therefore, are personal care compositions made from ingredients that are derived from natural sources, and methods of making and using them.

SUMMARY

Certain embodiments of the present invention provide personal care compositions comprising an extract of squash and/or pumpkin. These personal care compositions are for the hair and skin, including but not limited to, hair conditioner, shampoo, body lotion, body wash and face cream. The extract may be made from squash alone, from pumpkin alone, or from a combination of squash and pumpkin. The extracts are combined with a preservative. The personal care compositions further comprise a cosmetic base. The personal care compositions optionally further comprise fragrances, emulsifiers, thickeners, or surfactants or combinations thereof. Other embodiments provide methods of making the personal care compositions. Still other embodiments provide methods of using the personal care compositions for cleaning and/or moisturizing skin and/or hair. These personal care compositions provide beneficial effects to the skin and hair as reported by individuals who used the compositions.

DETAILED DESCRIPTION

Certain embodiments of the present invention provide personal care compositions comprising an extract of squash and/or pumpkin. In different embodiments, these personal care compositions are useful for treating the hair and skin, including but not limited to, hair conditioner, shampoo, body lotion, body wash and face cream. The extract of squash and/or pumpkin may be made from squash alone, from pumpkin alone, or from a combination of the squash and pumpkin. In one embodiment, the squash is a butternut squash. The personal care compositions further comprise cosmetic bases, preservatives, and optionally fragrances, emulsifiers, thickeners, or surfactants or combinations thereof. Other embodiments provide methods of making the personal care compositions. Still other embodiments provide methods of using the personal care compositions for cleaning and/or moisturizing skin and/or hair.

Certain embodiments of the present invention provide personal care compositions comprising a preservative and an extract of squash and/or pumpkin. The compositions further comprise cosmetic bases, preservatives, and optionally fragrances, emulsifiers, thickeners, or surfactants or combinations thereof. In certain embodiments, the composition is a shampoo for the hair. In some embodiments, the composition is a conditioner for the hair. In other embodiments, the composition is a cream for the skin, particularly the face. In other embodiments, the composition is a lotion for the hands and body. In still other embodiments, the composition is a body wash.

Compositions Comprising Squash and/or Pumpkin Extract

Extracts of squash and/or pumpkin for use in the composition contain the fruit, flesh and seeds of the squash and/or pumpkin and can be derived from different varieties and species. For example, squash and pumpkin species include *Cucurbita pepo, Cucurbita mixta, Cucurbita maxima*, and *Cucurbita moschata* and different varieties of these species. In one embodiment, the squash extract is derived from butternut squash. In one embodiment, the butternut squash extract is derived from a Waltham variety butternut squash. In other embodiments, the squash extract is derived from acorn squash, spaghetti squash, amber cup squash, hubbard squash, jarrandale squash or turban squash, or a combination thereof. In another embodiment, the pumpkin extract is derived from an "Old Timey" field pumpkin or an "Indian River" pie pumpkin, or a combination thereof. In some embodiments, the squash and/or pumpkins are harvested before they reach full maturity. For example, in one embodiment, the squash and/or pumpkins are harvested while still green. In another embodiment, the pumpkins and butternut squash are harvested between 60-110 days after planting. In still another embodiment, the pumpkins and butternut squash are harvested between 80-110 days after planting.

Other Ingredients

The disclosed personal care compositions comprise a cosmetic base composition and the squash and/or pumpkin extract including a preservative. Such cosmetic bases are commonly used in the making of personal care compositions and many versions are commercially available. Some examples of such cosmetic base compositions are provided in the examples of this patent application. Shampoo base was purchased from Bulk Apothecary (Streetsboro, Ohio, USA, commercially available online at www.bulkapothecary.com). Conditioner base for the hair was purchased from Bulk Apothecary (Streetsboro Ohio, USA, also commercially available online at bulkapothecary.com) or from New Directions Aromatics Inc., San Ramon, Calif. www.newdirectionsaromatics.com). Cream base was purchased from New Directions Aromatics Inc., 2129 Watercress Pl., San Ramon, Calif. 94583, USA, also commercially available online at newdirectionsaromatics.ca). The lotion base for the hands and body was purchased from Bulk Apothecary (Streetsboro Ohio, USA, also commercially available online at bulkapothecary.com). Body wash base was purchased from Bulk Apothecary (Streetsboro Ohio, USA, also commercially available online at bulkapothecary.com) or from New Directions Aromatics Inc., San Ramon, Calif. www.newdirectionsaromatics.com).

The compositions further comprise preservatives. Non-limiting examples of preservatives include benzyl alcohol dehydroacetic acid (benzyl alcohol DHA—Making Cosmetics (Renton, Wash. 98056, USA, also commercially available online at www.makingcosmetics.com)), phenonip (Clariant UK, Ltd., Leed, UK), and Liquid Germall® Plus (International Specialty Products, Wayne, N.J.), potassium benzoate or combinations thereof. Other preservatives, antimicrobials, antifungals and anti-mold compositions may be employed as known to one of ordinary skill in the art. Phenonip is a combination of phenoxyethanol, methylparaben, ethylparaben, butylparaben, propylparaben, and isobutylparaben. Liquid Germall® Plus is a combination of propylene glycol, diazolidinyl urea and iodopropynyl butylcarbamate. Many of these preservatives are commercially available from Making Cosmetics (Renton, Wash., US).

The compositions may further comprise fragrances, emulsifiers, thickeners, surfactants, or combinations thereof. Non-limiting examples of fragrances are honey, lavender oil and eucalyptus oil. Any commercially available honey may be used. For most examples in the present application, the honey was obtained from beekeeper B. J. Weeks of Ballground, Ga., USA. A non-limiting example of a surfactant is cocamide betaine (cocamidopropyl betaine). Glucose-T is an extremely non-ionic thickener for hair care and skin care products. Glucose-T is derived from corn. (CAS#9005-65-6 purchased from Making Cosmetics (Renton, Wash., US, PEG-120 methyl glucose trioleate, propylene glycol, water)

Non-limiting examples of thickeners include aloe vera gel, cranberry seed oil, and honey. These ingredients are optimally selected to improve the consistency of the compositions, to be rich in antioxidants and vitamins, and to impart a pleasant, natural scent to the claimed compositions. In other embodiments, the compositions comprise other ingredients optimally derived from natural sources, such as eucalyptus oil, lavender oil, olive oil, cinnamon oil, grapefruit oil, orange oil, cranberry seed oil, or other essential oils, honey, sea salt, vinegar, or aloe vera extract. In other embodiments, the compositions comprise Tripeptide 5 (palmitoyl tripeptide-5 glycerin) (MakingCosmetics Inc., Renton Wash.). Aloe vera extract was obtained from Making Cosmetics (Renton, Wash. 98056, USA, also commercially available online at www.makingcosmetics.com).

It is to be understood that other fragrances, emulsifiers, thickeners, surfactants, and preservatives may be employed as known to one of ordinary skill in the art.

Methods of Making the Personal Care Compositions
Preparation of Squash and/or Pumpkin Extract All the squash and/or pumpkin extracts described herein were made at room temperature. Sterilized containers and utensils were used, and the preparer cleaned and sterilized hands and wore sterile food preparation plastic gloves. The squash and/or pumpkin extracts were generally made with the following method: a) obtaining squash and/or pumpkin; b) removing the stem from the squash and/or pumpkin; c) dicing the squash and/or pumpkin to obtain fragments; d) juicing the squash and/or pumpkin fragments to obtain a liquid; e) straining the liquid to obtain the squash and/or pumpkin extract; f) adding preservative to the squash and/or pumpkin extract. At this stage, the squash and/or pumpkin extract with added preservative may be stored in sterile containers. The squash and/or pumpkin extract with added preservative is preferably stored in a refrigerator.

In yet another embodiment the present invention provides methods of making an extract of squash. Such methods include: obtaining squash; removing the stem, dicing squash to obtain fragments; juicing the squash fragments to obtain a liquid; and straining the liquid to obtain the squash extract. The preservative is then added to the extract.

In yet another embodiment the present invention provide methods of making an extract of pumpkin. Such methods include: obtaining pumpkin; removing the stem, slicing pumpkin to obtain fragments; juicing the pumpkin fragments to obtain a liquid; and straining the liquid to obtain the pumpkin extract. The preservative is then added to the extract.

In another embodiment, the pumpkin extract and the butternut squash extract may be prepared separately and then combined in a desired proportion to make a combined pumpkin and squash extract. The preservative may be added to the extract combined extracts or to each extract before combining the extracts.

In one embodiment the present invention provides methods of making an extract of butternut squash and pumpkin. Such methods include: obtaining butternut squash and/or pumpkin; removing the stem, slicing the butternut squash and pumpkin to obtain fragments; juicing the butternut squash and pumpkin fragments to obtain a liquid; and straining the liquid to obtain the butternut squash and pumpkin extract.

In another embodiment, the pumpkin extract and the butternut extract may be prepared separately and then combined in a desired proportion to make a combined pumpkin and butternut squash extract. The preservative may be added to the extract combined extracts or to each extract before combining the extracts.

In another specific embodiment the present invention provide methods of making an extract of butternut squash. Such methods include: obtaining butternut squash; removing the stem, slicing the butternut squash to obtain fragments; juicing the butternut squash fragments to obtain a liquid; and straining the liquid to obtain the butternut squash extract. The preservative is then added to the extract.

Other embodiments of the present invention provide methods of making personal care compositions comprising a base and an extract of squash and/or pumpkin. All the personal care compositions described herein were made at room temperature. Sterilized containers and utensils were used, and the preparer cleaned and sterilized hands and wore sterile food preparation plastic gloves. Such methods include: a) obtaining squash and/or pumpkin; b) removing the stem from the squash and/or pumpkin; c) dicing the squash and/or pumpkin to obtain fragments; d) juicing the squash and/or pumpkin fragments to obtain a liquid; e) straining the liquid to obtain the squash and/or pumpkin extract; f) adding preservative to the squash and/or pumpkin extract and g) mixing the squash and/or pumpkin extract with an amount of base at room temperature until combined. In some embodiments, the methods comprise the addition of other ingredients, such as, emulsifiers, surfactants, and fragrances. The additional ingredients may also be naturally derived ingredients.

Ingredients and Percentage Ranges of Specific Embodiments of Pumpkin and/or Squash Extract The compositions of the invention comprise an extract made of squash/and or pumpkin. In one embodiment, the extract may be made from 100% squash. In another embodiment, the extract may be made from 100% pumpkin. In other embodiments, the extract may be made from a combination of squash and pumpkin. All numbers in this paragraph are in volume percent (vol %). In one embodiment, the extract is made from a combination of 50% squash and 50% pumpkin. In another embodiment, the extract is made from a combination of 75% squash and 25% pumpkin. In another embodiment, the extract is made from a combination of 70% squash and 30% pumpkin. In another embodiment, the extract is made from a combination of 60% squash and 40% pumpkin.

All of these different ratios (50:50, 75:25, 70:30, and 60:40, squash:pumpkin) have been made and work. When the extract is made from a combination of squash and pumpkin, any amount of pumpkin between 0% and 100% and any amount of squash between 100% and 0% may be used. In other embodiments, the combined extract is made from about 1%, 5%, 10%, 15%, 20%, 25%, 30%, 35%, 40%, 45%, 50%, 55%, 60%, 65%, 70%, 75%, 80%, 85%, 90%, 95%, or 99% squash, and from about 1%, 5%, 10%, 15%, 20%, 25%, 30%, 35%, 40%, 45%, 50%, 55%, 60%, 65%, 70%, 75%, 80%, 85%, 90%, 95%, or 99% pumpkin for a total of 100%. It is to be understood that any ratio of pumpkin to squash may be used to prepare the extract. Once the extract has been prepared, other ingredients may be added to the extract, such as a preservative. In one embodiment, the preservative benzyl alcohol DHA is added to the extract. In another embodiment, phenonip and germall are added as preservatives, alone or in combination, to the extract. In one embodiment, the preservative potassium benzoate is added to the extract. In yet another embodiment, phenonip, germall and potassium benzoate are added as preservatives to the extract.

In a specific embodiment, the squash is butternut squash and the compositions of the invention comprise an extract made of butternut squash/and or pumpkin. In one embodiment, the extract may be made from 100% butternut squash. In another embodiment, the extract may be made from 100% pumpkin. In other embodiments, the extract may be made from a combination of butternut squash and pumpkin. In one embodiment, the extract is made from a combination of 50% butternut squash and 50% pumpkin. In another embodiment, the extract is made from a combination of 75% butternut squash and 25% pumpkin. In another embodiment, the extract is made from a combination of 70% butternut squash and 30% pumpkin. In another embodiment, the extract is made from a combination of 60% butternut squash and 40% pumpkin. All of these different ratios (50:50, 75:25, 70:30, and 60:40, butternut squash:pumpkin) have been made and work. When the extract is made from a combination of butternut squash and/or pumpkin, any amount of pumpkin between 0% and 100% and any amount of butternut squash between 100% and 0% may be used. In other embodiments, the combined extract is made from about 1%, 5%, 10%, 15%, 20%, 25%, 30%, 35%, 40%, 45%, 50%, 55%, 60%, 65%, 70%, 75%, 80%, 85%, 90%, 95%, or 99% butternut squash, and from about 1%, 5%, 10%, 15%, 20%, 25%, 30%, 35%, 40%, 45%, 50%, 55%, 60%, 65%, 70%, 75%, 80%, 85%, 90%, 95%, or 99% pumpkin for a total of 100%. It is to be understood that any ratio of butternut pumpkin to squash may be used to prepare the extract. Once the extract has been prepared, other ingredients may be added to the extract, such as a preservative. In one embodiment, the preservative benzyl alcohol DHA is added to the extract. In another embodiment, phenonip and germall are added as preservatives, alone or in combination, to the extract. In one embodiment, the preservative potassium benzoate is added to the extract. In yet another embodiment, phenonip, germall and potassium benzoate are added as preservatives to the extract.

In preparing the extract of squash, the extract of pumpkin, or the combined extract of squash and pumpkin, stalks were removed from the squash and from the pumpkin which were then diced into small pieces, and run through a juicer to obtain the liquid extract of squash, pumpkin or squash and pumpkin. The liquid extract of squash, pumpkin, or squash and pumpkin, was then put through a strainer to remove any traces of the pulp, preservative was added to the strained liquid extract which was then placed in a sterile container.

Shampoo

One specific embodiment of the present invention is a shampoo made in accordance with the formula shown in Table 1. The shampoo may also be made with the listed ingredients in the quantities covered by the percentage range.

TABLE 1

Shampoo Formula

| Percentage and Range (vol %) | Ingredient |
|---|---|
| 15% (5-25%) | Pumpkin and/or Butternut Squash extract (including a preservative such as benzyl alcohol DHA, potassium benzoate, or phenonip and germall, or a combination thereof such as potassium benzoate, phenonip and germall) |
| 10% (0-20%) | Pumpkin Blossom Honey & Mountain Honey Blend |
| 2.5% (0-10%) | 10x Concentrated *Aloe Vera* Extract |
| 1.5% (0-10%) | *Eucalyptus* Oil |
| 1% (0-10%) | Lavender Oil |
| 5% (0-15%) | Sea Salt |
| 65% (55-75%) | Shampoo Base (Water, decyl glucoside, cocamide betaine, lauramide diethanolamine (DEA), lauryl glucoside, disodium ethylenediaminetetraacetic acid (EDTA), methylchlorisothiazolinone, methylisothiazolinone, citric acid, sodium chloride, vitamin A, vitamin D, vitamin E, hemp oil, avocado oil, coconut oil) |

In this embodiment, the unscented shampoo base was obtained from Bulk Apothecary (Ohio, USA, commercially available online at www.bulkapothecary.com).

Hair Conditioner

Another specific embodiment of the present invention is a conditioner made in accordance with the formula shown in Table 2. The conditioner may also be made with the listed ingredients in the quantities covered by the percentage range.

TABLE 2

Hair Conditioner Formula

| Percentage and Range (vol %) | Ingredient |
|---|---|
| 15% (5-25%) | Pumpkin and/or Butternut Squash extract (including a preservative such as benzyl alcohol DHA, potassium benzoate, or phenonip and germall, or a combination thereof such as potassium benzoate, phenonip and germall) |
| 10% (5-25%) | Pumpkin Blossom Honey |
| 5% (0-15%) | 10x *Aloe Vera* Extract |
| 5% (0-15%) | Cyclo-dimethicone |
| 3.5% (0-10%) | *Eucalyptus* Oil |
| 1.5% (0-10%) | Lavender Oil |
| 5% (0-15%) | Cocamide betaine |
| 55% (45-65%) | Conditioner base (Water, glycerin, emulsifying wax, mineral oil, quanternium-7, polyvinylpyrrolidone (pvp), glyceryl stearate, stearalkonium chloride, ethoxydiglycol, propylene glycol, butylene glycol, extracts of *matricaria*, nettle, birch sap, *arnica*, *cinchona*, and birch leaf, potassium sorbate, sodium benzoate, imidazolidinyl urea) |

In this specific embodiment, the conditioner base (conditioner base ultra premium was obtained from New Directions Aromatics (New Directions Aromatics Inc., 2129 Watercress Pl., San Ramon, Calif. 94583, USA, also commercially available online at newdirectionsaromatics.ca)).

Face Cream

Another specific embodiment is a face cream made in accordance with the formula shown in Table 3. The face cream may also be made with the listed ingredients in the quantities covered by the percentage range.

TABLE 3

Face Cream Formula

| Percentage and Range (vol %) | Ingredient |
|---|---|
| 30% (20-40%) | Pumpkin and/or Butternut Squash extract (including a preservative such as benzyl alcohol DHA, potassium benzoate, or phenonip and germall, or a combination thereof such as potassium benzoate, phenonip and germall) |
| 10% (0-20%) | Pumpkin Blossom Honey & Mountain Honey Blend |
| 10% (0-20%) | 10x Concentrated Aloe Vera Extract |
| 10% (0-20%) | Cranberry Seed Oil |
| 4% (0-13%) | Gel Maker Emulsifier |
| 4% (0-12%) | Eucalyptus oil |
| 2% (0-12%) | Lavender oil |
| 30% (20-40%) | Face Cream Base (Water, Cetearyl Alcohol, Ceteareth-20 Glycerin, Shea butter (*Butyrospermum Parkii*), Palm Oil Coconut (*Cocos Nucifera*), Oil Glyceryl Monostearate, Sunflower (*Helianthus Annus*) Seed Oil Beeswax (Cera Alba), Dimethicone, Phenoxyethanol, Carbomer, Tocopherol (Vitamin E), Sodium Citrate |

In this embodiment, the face cream base (Cream Base ultra premium) and cranberry seed oil were purchased from New Directions Aromatics (New Directions Aromatics Inc., 2129 Watercress Pl., San Ramon, Calif. 94583, USA, also commercially available online at newdirectionsaromatics.ca). Any commercially available honey may be used.

Hand and Body Lotion

Yet another specific embodiment of the invention is a hand and body lotion made in accordance with the formula shown in Table 4. The hand and body lotion may also be made with the listed ingredients in the quantities covered by the percentage range.

TABLE 4

Hand and Body Lotion Formula

| Percentage and Range (vol %) | Ingredient |
|---|---|
| 17% (7-27%) | Pumpkin and/or Butternut Squash extract (including a preservative such as benzyl alcohol DHA, potassium benzoate, or phenonip and germall, or a combination thereof such as potassium benzoate, phenonip and germall) |
| 6% (0-16%) | Pumpkin Blossom & Mountain Blend Honey |
| 6% (0-16%) | 10x Concentrated *Aloe Vera* Extract |
| 6% (0-16%) | Cranberry Seed Oil |
| 0.67% (0-10%) | *Eucalyptus* Oil |
| 0.33% (0-10%) | Lavender Oil |
| 64% (54-74%) | Body Lotion Base (Water, hemp oil, propylene glycol, stearic acid, cetyl alcohol, glyceryl stearate, extracts of avocado, chamomile, lavender, sage and witch hazel, dimethicone, allantoin, carbomer, methylparaben, disodium ethylenediaminetetraacetic acid (EDTA), triethanolamine, imidazolidinyl urea, propyl paraben, aloe vera, and vitamin E) |

In this embodiment, the hand and body lotion base (unscented hand and body lotion base was obtained from Bulk Apothecary (Ohio, USA, also commercially available online at www.bulkapothecary.com)). Any commercially available honey may be used.

Body Wash

Another specific embodiment of the invention is a body wash made in accordance with the formula shown in Table 5. The body wash may also be made with the listed ingredients in the quantities covered by the percentage range.

TABLE 5

Body Wash Formula

| Percentage and Range (vol %) | Ingredient |
|---|---|
| 19% (9-29%) | Pumpkin and/or Butternut Squash extract (including a preservative such as benzyl alcohol DHA, potassium benzoate, or phenonip and germall, or a combination thereof such as potassium benzoate, phenonip and germall) |
| 6% (0-16%) | 10x Concentrated *Aloe Vera* Extract |
| 6% (0-16%) | Pumpkin Blossom & Mountain Blend Honey |
| 2% (0-10%) | Lavender Oil |
| 67% (57-77%) | Body Wash Base (water, ammonium lauryl sulfate, ammonium laureth sulfate, lauramide diethanolamine (DEA), lauryl glucoside, disodium ethylenediaminetetraacetic acid (EDTA), methylchlorisothiazolinone, methylisothiazolinone, citric acid, sodium chloride, vitamin A, vitamin D, vitamin E) |

In this specific embodiment, the body wash base (unscented shower gel/body wash base was obtained from New Directions Aromatics (New Directions Aromatics Inc., 2129 Watercress Pl., San Ramon, Calif. 94583, USA, also commercially available online at newdirectionsaromatics.ca)). Any commercially available honey may be used.

In other embodiments, as shown in additional examples, the percentage (vol %) of squash and/or pumpkin extract in various personal care compositions may be different than those shown in Tables 1-5. The personal care compositions may contain at least 5%, 10%, 15%, 20%, 25%, 30%, 35% or 40% (vol %) of squash and/or pumpkin extract. In separate embodiments, the personal care compositions may contain 5%-50%, 10%-40% or 15%-35% (vol %) of squash and/or pumpkin extract. Specific ranges of squash and/or pumpkin extract in conditioner may be 5-25%, or 10-20%. Ranges of squash and/or pumpkin extract in body wash may be 10-50%, 15-40% or 20-35%. Ranges of squash and/or pumpkin extract in face cream may be 20-60%, 25-50%, or 30-45%. Ranges of squash and/or pumpkin extract in lotion may be 10-50%, 20-40% or 25-35%. Ranges of squash and/or pumpkin extract in shampoo may be 10-45%, 15-40% or 20-35%. It is to be understood that the actual volume percentage may also be any number within these ranges. Some specific embodiments are provided in examples 6 to 15.

Methods of Using the Personal Care Compositions

Still other embodiments of the present invention provide methods of using personal care compositions comprising a base and an extract of squash and pumpkin in order to clean and/or moisturize the skin and/or hair. These methods may include methods of using the compositions in the form of shampoo, conditioner, face cream, hand and body lotion, or body wash. The compositions may be used as one would normally use other hair care and skin care products.

The compositions of the present invention are designed to provide excellent care for the skin and hair using ingredients derived from natural sources. Some of the objectives of the present invention are: to improve the quality of hair so that it is healthier, shinier, and/or more manageable; to improve the cleanliness, moisture, tone, and smoothness of the skin of the face and body; and to provide products with a pleasant scent.

The following examples will serve to further illustrate the present invention without, at the same time, however, constituting any limitation thereof. On the contrary, it is to be clearly understood that resort may be had to various embodiments, modifications and equivalents thereof which, after reading the description herein, may suggest themselves to those skilled in the art without departing from the spirit of the invention.

EXAMPLE 1

Shampoo
Formula

A shampoo was made in accordance with the formula shown in Table 6.

TABLE 6

Shampoo Formula

| Quantity (by vol.) (fluid ounces) (ml) | Volume % of total | Ingredient |
|---|---|---|
| 2.25 oz. (66.5 ml) | 17 | Butternut Squash:Pumpkin extract (with benzyl alcohol DHA) |
| 1.5 oz. (44.4 ml) | 11 | Pumpkin Blossom Honey & Mountain Honey Blend |
| 0.5 oz. (14.8 ml) | 3.5 | 10x Concentrated *Aloe Vera* Extract |
| 0.125 oz. (3.7 ml) | 0.9 | *Eucalyptus* Oil |
| 0.062 oz. (1.93 ml) | 0.4 | Lavender Oil |
| 0.5 oz. (14.8 ml) | 3.6 | Sea Salt |
| 9 oz. (266.2 ml) | 64 | Shampoo Base (Water, decyl glucoside, cocamide betaine, lauramide diethanolamine (DEA), lauryl glucoside, disodium ethylenediaminetetraacetic acid (EDTA), methylchlorisothiazolinone, methylisothiazolinone, citric acid, sodium chloride, vitamin A, vitamin D, vitamin E, hemp oil, avocado oil, coconut oil) |
| Total 13.9 oz. (411 ml) | 100 | |

Method of Making the Shampoo

The shampoo was made in accordance with the following method.
1. 11.2 fluid ounces (331.1 ml) of butternut squash and 4.8 fluid ounces (141.9 ml) of pumpkin were obtained to make the butternut squash and pumpkin extract as described above.
2. Approximately 2 fluid ounces (59 ml) of benzyl alcohol DHA was added to every quart (946.4 ml) of strained butternut squash and pumpkin extract.
3. In a separate sterile container, the honey, aloe vera extract, lavender oil, eucalyptus oil, and sea salt were added sequentially and thoroughly mixed. The butternut squash and pumpkin extract was then added and mixed thoroughly using a mechanical mixer with a whisk attachment. The shampoo base was added to the mixture and mixed using the mechanical mixer until it was smooth. The shampoo was then distributed into 8 individual bottles, each containing about 355 ml (12 fluid ounces).

Results of Using Shampoo

Three individuals tested the shampoo by using it instead of their normal shampoo. After four weeks of regularly using the shampoo to clean her hair, one individual reported that the texture of her hair was softer and that her hair was easier to manage. Another person noted that her hair was shinier and stated that she enjoyed the scent of her hair. A third individual stated that her hair had more body and volume after using the shampoo, and also noted that her hair was shinier.

EXAMPLE 2

Hair Conditioner
Formula

A conditioner was made in accordance with the formula shown in Table 7.

TABLE 7

Conditioner Formula

| Quantity (by vol.) (fluid ounces) (ml) | Volume % of total | Ingredient |
|---|---|---|
| 2.25 oz. (66.5 ml) | 14.8 | Butternut Squash:Pumpkin extract (with benzyl alcohol DHA) |
| 1.5 oz. (44.4 ml) | 9.9 | Pumpkin Blossom Honey |
| 0.75 oz. (22.2 ml) | 4.9 | 10x *Aloe Vera* Extract |
| 1 oz. (29.6 ml) | 6.6 | Cyclo-dimethicone |
| 0.125 oz. (3.7 ml) | 0.8 | *Eucalyptus* Oil |
| 0.062 oz. (1.84 ml) | 0.4 | Lavender Oil |
| 1 oz. (29.6 ml) | 6.6 | Cocamide betaine |
| 8.5 oz. (251.4 ml) | 56 | Conditioner base (Water, glycerin, emulsifying wax, mineral oil, quanternium-7, polyvinylpyrrolidone, glyceryl stearate, stearalkonium chloride, ethoxydiglycol, propylene glycol, butylene glycol, extracts of *matricaria*, nettle, birch sap, *arnica*, *cinchona*, and birch leaf, potassium sorbate, sodium benzoate, imidazolidinyl urea) |
| Total 15.18 oz (448.9 ml) | 100 | |

Method of Making the Conditioner

The conditioner was made in accordance with the following method.
1. 11.2 fluid ounces (331.1 ml) of butternut squash and 4.8 fluid ounces (141.9 ml) of pumpkin were obtained to make the butternut squash and pumpkin extract as described above.
2. Approximately 2 fluid ounces (59 ml) of benzyl alcohol DHA was added to every quart (946.4 ml) of strained butternut squash and pumpkin extract.
3. In a separate sterile container, the honey, aloe vera extract, lavender oil, eucalyptus oil, cyclo-dimethicone, and cocamide betaine were added sequentially and thoroughly mixed. The butternut squash and pumpkin extract was then added and mixed thoroughly using a mechanical mixer with a whisk attachment.
4. The conditioner base was added to the mixture and mixed with the mechanical mixer until it was smooth.

The conditioner was then distributed into individual bottles.

Results of Using the Conditioner

The conditioner was tested by two individuals that used the conditioner instead of their normal hair conditioner. One person noted that the conditioner smoothed and tamed her hair and made it easier to comb. She also stated that the conditioner moisturized and hydrated her hair. Another person also stated that the conditioner made her hair smoother and more manageable. She also stated that using the conditioner prevented her hair from tangling.

EXAMPLE 3

Face Cream
Formula

A face cream was made in accordance with the formula shown in Table 8.

TABLE 8

Face Cream Formula

| Quantity (by vol.) (fluid ounces) (ml) | Volume % of total | Ingredient |
|---|---|---|
| 2.25 oz. (66.5 ml) | 32.9 | Butternut Squash:Pumpkin extract (with benzyl alcohol DHA) |
| 0.75 oz. (22.2 ml) | 10.6 | Pumpkin Blossom Honey & Mountain Blend |
| 0.75 oz. (22.2 ml) | 10.6 | 10x Concentrated *Aloe Vera* Extract |
| 0.75 oz. (22.2 ml) | 10.6 | Cranberry Seed Oil |
| 0.25 oz. (7.4 ml) | 3.5 | Gel Maker Emulsifier |
| 0.125 oz. (3.7 ml) | 1.8 | *Eucalyptus* oil |
| 0.062 oz. (1.84 ml) | 0.9 | Lavender oil |
| 2.125 oz. (62.8 ml) | 30.1 | Face Cream Base (Water, Cetearyl Alcohol, Ceteareth-20 Glycerin, Shea butter (*Butyrospermum Parkii*), Palm Oil Coconut (*Cocos Nucifera*), Oil Glyceryl Monostearate, Sunflower (*Helianthus Annus*) Seed Oil Beeswax (*Cera Alba*), Dimethicone, Phenoxyethanol, Carbomer, Tocopherol (Vitamin E), Sodium Citrate |
| Total 7.06 oz. (208.8 ml) | 100 | |

Method of Making the Face Cream

The face cream was made in accordance with the following method.

1. 11.2 fluid ounces (331.1 ml) of butternut squash and 4.8 fluid ounces (141.9 ml) of pumpkin were obtained to make the butternut squash and pumpkin extract as described above.

2. Approximately 2 fluid ounces (59 ml) of benzyl alcohol DHA was added to every quart (946.4 ml) of strained butternut squash and pumpkin extract.

3. In a separate sterile container, the honey, aloe vera extract, lavender oil, eucalyptus oil, cranberry seed oil, and gel maker emulsifier were thoroughly mixed. The butternut squash and pumpkin extract was then added and mixed thoroughly using a mechanical mixer with a whisk attachment.

4. The face cream base was added to the mixture and mixed with the mechanical mixer until it was smooth.

The face cream was then distributed into individual bottles.

Results of Using the Face Cream

Three individuals tested the face cream by using it instead of their normal face creams and/or moisturizers. After using the face cream, one person noted that her skin was better moisturized, and that dry patches on her cheeks had disappeared. Another person stated that her skin appeared tighter and that she believed the face cream had caused fine wrinkles and blemishes to disappear. She also felt that the face cream was very moisturizing for her skin. A third person stated that the cream kept her face moisturized without making her skin oily, and noted that wrinkles and brown spots on her face were less noticeable after using the face cream.

EXAMPLE 4

Hand and Body Lotion

Formula

A hand and body lotion was made in accordance with the formula shown in Table 9.

TABLE 9

Hand and Body Lotion Formula

| Quantity (by vol.) (fluid ounces) (ml) | Volume % of total | Ingredient |
|---|---|---|
| 2.25 oz. (66.5 ml) | 17 | Butternut Squash:Pumpkin extract (with benzyl alcohol DHA) |
| 0.75 oz. (22.2 ml) | 5.7 | Pumpkin Blossom & Mountain Blend Honey |
| 0.75 oz. (22.2 ml) | 5.7 | 10x Concentrated *Aloe Vera* Extract |
| 0.75 oz. (22.2 ml) | 5.7 | Cranberry Seed Oil |
| 0.125 oz. (3.7 ml) | 0.9 | *Eucalyptus* Oil |
| 0.062 oz. (1.84 ml) | 0.47 | Lavender Oil |
| 8.5 oz. (251.3 ml) | 64.4 | Body Lotion Base (Water, hemp oil, propylene glycol, stearic acid, cetyl alcohol, glyceryl stearate, extracts of avocado, chamomile, lavender, sage and witch hazel, dimethicone, allantoin, carbomer, methylparaben, disodium EDTA, triethanolamine, imidazolidinyl urea, propyl paraben, *aloe vera*, and vitamin E) |
| Total 13.19 oz. (390.1 ml) | 100 | |

Method of Making the Hand and Body Lotion

The hand and body lotion was made in accordance with the following method.

1. 11.2 fluid ounces (331.1 ml) of butternut squash and 4.8 fluid ounces (141.9 ml) of pumpkin were obtained to make the butternut squash and pumpkin extract as described above.

2. Approximately 2 fluid ounces (59 ml) of benzyl alcohol DHA was added to every quart (946.4 ml) of strained butternut squash and pumpkin extract.

3. In a separate sterile container, the honey, aloe vera extract, lavender oil, eucalyptus oil, and cranberry seed oil were added sequentially and thoroughly mixed. The butternut squash and pumpkin extract was then added and mixed thoroughly using a mechanical mixer with a whisk attachment.

4. The hand and body lotion base was added to the mixture and mixed with the mechanical mixer until it was smooth.

The hand and body lotion was then distributed into individual bottles.

Results of Using the Hand and Body Lotion

Three individuals tested the hand and body lotion by using it instead of their normal hand and body lotions. After using the hand and body lotion, one person stated that it had improved her skin dramatically. She noted that the lotion instantly provided moisture upon application, and that her skin stayed moisturized throughout the day. Another person stated that her skin felt softer and smoother and looked healthier. She also stated that her skin was well moisturized by the hand and body lotion. A third person stated that the lotion made her skin soft and smooth and that her skin stayed moisturized all day. She also stated that the lotion penetrated the skin well, but that it let the skin "breathe".

EXAMPLE 5

Body Wash

Formula

A body wash was made in accordance with the formula shown in Table 10.

TABLE 10

Body Wash Formula

| Quantity (by vol.) (fluid ounces) (ml) | Volume % of total | Ingredient |
|---|---|---|
| 2.25 oz. (66.5 ml) | 19 | Butternut Squash:Pumpkin extract (with benzyl alcohol DHA) |
| 0.75 oz. (22.2 ml) | 6 | 10x Concentrated *Aloe Vera* Extract |
| 0.75 oz. (22.2 ml) | 6 | Pumpkin Blossom & Mountain Blend Honey |
| 0.062 oz. (1.84 ml) | 1.0 | Lavender Oil |
| 8.0 oz. (236.5 ml) | 68 | Body Wash Base (Water, ammonium lauryl sulfate, ammonium laureth sulfate, lauramide diethanolamine (DEA), lauryl glucoside, disodium ethylenediaminetetraacetic acid (EDTA), methychlorisothiazolinone, methylisothiazolinone, citric acid, sodium chloride, vitamin A, vitamin D, vitamin E (bulkapothecary.com, Bulk Apothecary Streetsboro Ohio, 44241) |
| Total 11.8 oz. (349.2 ml) | 100 | |

Method of Making the Body Wash

The body wash was made in accordance with the following method.

1. 11.2 fluid ounces (331.1 ml) of butternut squash and 4.8 fluid ounces (141.9 ml) of pumpkin were obtained to make the butternut squash and pumpkin extract as described above.

2. Approximately 2 fluid ounces (59 ml) of benzyl alcohol DHA was added to every quart (946.4 ml) of strained butternut squash and pumpkin extract.

3. In a separate sterile container, the honey, aloe vera extract, and lavender oil were added sequentially thoroughly mixed. The butternut squash and pumpkin extract was then added and mixed thoroughly using a mechanical mixer with a whisk attachment.

4. The body wash base was then added to the mixture and mixed with the mechanical mixer until it was smooth.

The body wash was then distributed into individual bottles.

Results of Using the Body Wash

The body wash was tested by three individuals. After using the body wash for four weeks, one individual noticed softer skin. She stated that she preferred the scent of the body wash as compared to other body washes that had a harsher scent. Another person stated that her skin felt smoother and tighter after using the body wash, and stated that she enjoyed the scent and the clean feeling that the body wash provided. A third person stated that the body wash lathered well, left her skin feeling clean and smooth all day, and moisturized and "refreshed" her skin.

EXAMPLE 6

Conditioner
Formula

A conditioner was made in accordance with the formula shown in Table 11.

TABLE 11

| Quantity (by vol.) | Volume % of total | Ingredient |
|---|---|---|
| 8 cups (1.892 L) | 62.1 | Conditioner Base |
| 2 cups (473 ml) | 15.53 | Butternut Squash:Pumpkin extract containing 1% liquid germall plus (vol %) and 1% phenonip (vol %) |
| ½ cup (118 ml) | 3.9 | *Aloe Vera* extract |
| 2 cups (473 ml) | 15.5 | Cyclo-dimethicone |
| ¼ cup (59.2 ml) | 1.9 | Olive Oil |
| ⅛ cup (29.6 ml) | 1.0 | Apple Cider Vinegar |
| Total 3045 ml | 100 | |

Method of Making the Conditioner

The conditioner was made in accordance with the following method.

1. 11.2 fluid ounces (331.1 ml) of butternut squash and 4.8 fluid ounces (141.9 ml) of pumpkin were obtained to make the butternut squash and pumpkin extract as described above.

2. Germall and Phenonip were added to the strained butternut squash and pumpkin extract each at 1% by volume of the extract.

3. In a separate sterile container, the butternut squash and pumpkin extract including Germall and Phenonip, and conditioner base were thoroughly mixed using a mechanical mixer with a whisk attachment. Next, the aloe vera extract, cyclo-dimethicone, olive oil and apple cider vinegar were added sequentially and mixed well with a mechanical mixer. The body lotion was then distributed into 8 individual bottles, each containing about 355 ml (12 fluid ounces).

EXAMPLE 7

Body Lotion
Formula

A body lotion was made in accordance with the formula shown in Table 12.

TABLE 12

| Quantity (by vol.) | Volume % of total | Ingredient |
|---|---|---|
| 10 cups (2.365 L) | 58.6 | Body Lotion base |
| 5 cups (1.183 L) | 30.3 | Butternut Squash:Pumpkin extract containing 1% liquid germall plus & 1% phenonip |
| ½ cup (118 ml) | 2.9 | Gel Maker - EMU |
| ⅓ cup (78.1 ml) | 1.9 | Cranberry Seed Oil |
| ⅓ cup (78.1 ml) | 1.9 | Cyclo-Dimethicone |
| ¼ cup (59.1 ml) | 1.5 | Honey |
| ½ teaspoon (2.5 ml) | 0.06 | Citric acid powder |
| ½ teaspoon (2.5 ml) | 0.06 | Cinnamon Oil |
| 4 teaspoons (19.7 ml) | 0.49 | Orange Oil |
| 2 teaspoons (9.86 ml) | 0.24 | Grapefruit Oil |
| ½ cup (118 ml) | 2.0 | *Aloe Vera* extract |
| Total 4034 ml | 100 | |

Method of Making the Body Lotion

The body lotion was made in accordance with the following method.

1. 11.2 fluid ounces (331.1 ml) of butternut squash and 4.8 fluid ounces (141.9 ml) of pumpkin were obtained to make the butternut squash and pumpkin extract as described above.

2. Germall and Phenonip were added to the strained butternut squash and pumpkin extract, each at 1% by volume of the extract.

3. In a separate sterile container, the butternut squash and pumpkin extract including liquid Germall plus and Phenonip, and body lotion base were thoroughly mixed using a mechanical mixer with a whisk attachment.

4. Next, the gel maker-EMU, cranberry seed oil, and cyclodimethicone were added sequentially and mixed well with a mechanical mixer set to medium speed. Next the honey, citric powder, cinnamon oil, orange oil, grapefruit oil and Aloe vera extract were added and mixed in the order provided. The body lotion was then distributed into individual bottles.

Results of Using the Body Lotion

One individual reported that after using the lotion two times, her skin felt softer and dark spots appeared to fade. Another individual used the body lotion for several months and reported that it eliminated razor rash on her legs and left no oil residue on her skin.

EXAMPLE 8

Face Cream
Formula

A face cream was made in accordance with the formula shown in Table 13.

TABLE 13

| Quantity (by vol.) | Volume % of total | Ingredient |
| --- | --- | --- |
| 4 cups (946 ml) | 40 | Face Cream base |
| 4 cups (946 ml) | 40 | Butternut Squash:Pumpkin extract containing 1% Liquid Germall plus & 1% Phenonip |
| ½ cup (118 ml) | 5 | Honey |
| ½ cups (118 ml) | 5 | *Aloe Vera* |
| ½ cup (118 ml) | 5 | Cranberry Seed Oil |
| ⅓ cup (78.1 ml) | 3.3 | Gel Maker - EMU |
| 2 teaspoons (9.86 ml) | 0.42 | Citric Acid powder |
| ½ teaspoon (2.46 ml) | 0.1 | Cinnamon Oil |
| 2 tablespoons (29.57 ml) | 1.2 | Tripeptide 5 (palmitoyl tripeptide-5 glycerin) |
| 1 teaspoon (4.93 ml) | 0.2 | Orange Oil |
| Total 2371 ml | 100 | |

Yields 19 4 fluid oz (118.3 ml) jars.

Method of Making the Face Cream

The face cream was made in accordance with the following method.

1. 11.2 fluid ounces (331.1 ml) of butternut squash and 4.8 fluid ounces (141.9 ml) of pumpkin were obtained to make the butternut squash and pumpkin extract as described above.
2. Germall and Phenonip were added to the strained butternut squash and pumpkin extract, each at 1% by volume of the extract.
3. In a separate sterile container, the butternut squash and pumpkin extract including Germall and Phenonip, honey, aloe vera extract, cranberry seed oil, and face cream base were added sequentially thoroughly mixed using a mechanical mixer with a whisk attachment. The mixer was set at medium speed for about 30 seconds.
4. Next, the gel maker-EMU, citric acid, cinnamon oil, tripeptide 5, orange oil were added sequentially and mixed well
5. The face cream was then distributed into 19 individual jars each containing 4 fluid oz. (118.3 ml).

Results of Using the Face Cream

One individual reported that after using the face cream, her face felt moisturized but not oily. She also reported that dark spots appeared to fade.

EXAMPLE 9

Body Wash
Formula

A body wash was made in accordance with the formula shown in Table 14.

TABLE 14

| Quantity (by vol.) | Volume % of total | Ingredient |
| --- | --- | --- |
| 8 cups (1.892 L) | 59 | body wash base |
| 4 cups (946 ml) | 30 | Butternut Squash:Pumpkin extract containing 1% Liquid Germall Plus & 1% Phenonip |
| ¾ cup (177 ml) | 5.5 | cocamide betaine |
| ½ cup (118 ml) | 3.7 | Honey |
| ¼ cup (59.1 ml) | 1.8 | Glucose-T |
| 2 teaspoons (9.9 ml) | 0.3 | Pink lemonade scent |
| Total 3202 ml | 100% | |

Pink lemonade scent purchased from Crafter's Choice, Pink Lemonade Fragrance Oil 446, Crafter's Choice Brands LL Broadview Heights, OH)

Method of Making the Body Wash

The body wash was made in accordance with the following method.

1. 11.2 fluid ounces (331.1 ml) of butternut squash and 4.8 fluid ounces (141.9 ml) of pumpkin were obtained to make the butternut squash and pumpkin extract as described above.
2. Germall and Phenonip were added to the strained butternut squash and pumpkin extract, each at 1% by volume of the extract.
3. In a separate sterile container, the butternut squash and pumpkin extract including Germall and Phenonip, body wash base, cocamidopropyl betaine (cocamide betaine), honey, glucose-T, and scent were added individually and mixed in the order provided. The body wash was then distributed into 9 individual bottles, each containing 12 oz. (354.9 ml).

Results of Using the Body Wash

Two individuals reported the following results. "I use the body wash every night and I can really feel the difference in the softness of my skin. I also love the scent a strong scent, but at the same time not an overwhelming scent." "The body wash lathers really well, smells great and doesn't leave my skin dry and flakey it makes it soft and smooth."

EXAMPLE 10

Shampoo
Formula

A shampoo was made in accordance with the formula shown in Table 15.

TABLE 15

| Quantity (by vol.) | Volume % of total | Ingredient |
| --- | --- | --- |
| 8 cups (1.893 L) | 57 | Shampoo base |
| 4 cups (946 ml) | 28 | Butternut Squash:Pumpkin extract containing 1% liquid germall plus (vol %) and 1% phenonip (vol %) |
| 1 cup (236.5 ml) | 7.1 | cocamide betaine |
| ½ cup (118.3 ml) | 3.6 | *Aloe Vera* extract |
| ½ cup (118.3 ml) | 3.6 | Honey |
| 2 teaspoons (9.9 ml) | 0.3 | Fragrance scented oil - pink lemonade |
| Total 3221 ml | 100% | |

Method of Making the Shampoo

The shampoo was made in accordance with the following method.

1. 11.2 fluid ounces (331.1 ml) of butternut squash and 4.8 fluid ounces (141.9 ml) of pumpkin were obtained to make the butternut squash and pumpkin extract as described above.
2. Germall and Phenonip were added to the strained butternut squash and pumpkin extract, each at 1% by volume of the extract.
3. In a separate sterile container, the butternut squash and pumpkin extract including Germall and Phenonip, shampoo base, cocamidopropyl betaine, aloe vera extract, honey, and scented oil were added individually and sequentially and mixed in the order provided. A mechanical mixer was used at medium speed.
4. The shampoo was then distributed into individual bottles. This produced 8-12 fluid oz. (355 ml) bottles.

Results of Using the Shampoo

One individual reported that the shampoo lathered well, the scent was nice not overwhelming and skin was left feeling soft and smooth, not dry and flakey.

EXAMPLE 11

Body Wash
Formula

A body wash was made in accordance with the formula shown in Table 16.

TABLE 16

| Quantity (by vol.) | Volume % of total | Ingredient |
| --- | --- | --- |
| 8 cups (1.892 L) | 59 | body wash base |
| 4 cups (946 ml) | 29 | Butternut Squash:Pumpkin extract (70%:30%) containing 1% liquid germall plus (vol %), 1% phenonip (vol %) & 1% potassium benzoate |
| 2 tablespoons (29.6 ml) | 0.9 | potassium ascorbate |
| ¾ cup (177 ml) | 5.5 | cocamide betaine |
| ½ cup (118 ml) | 3.7 | Honey |
| ¼ cup (59 ml) | 1.8 | Glucose-T |
| 2 teaspoon (9.9 ml) | 0.3 | Fragrance Scent pink lemonade |
| Total 3232 ml | 100% | |

The butternut squash/pumpkin extract containing 1% germall, 1% phenonip and 1% potassium benzoate was added to the body wash base and mixed well with a mechanical mixer. Next potassium ascorbate was added and mixed well. Then the cocamide betaine, honey, glucose-T and scent were sequentially added and mixed well. This produced 9-12 oz. (355 ml) bottles.

Results of Using the Body Wash

Five individuals provided the following reports. "I love the way this lathers. It also leaves me feel fresh and clean when I get out of the shower." "It lathers like it should, smells amazing and doesn't leave my skin feeling dry and flakey." "When I use the body wash and body lotion together, my skin stays moisturized all day long, and the scent combined is amazing but not too strong." "I use this every night and I can really feel a difference in my skin since I started using it. Also great to shave my legs with!" "I use this every day and the scent is not too strong but strong enough to smell fresh and clean after I shower."

EXAMPLE 12

Body Lotion
Formula

A body lotion was made in accordance with the formula shown in Table 17.

TABLE 17

| Quantity (by vol.) | Volume % of total | Ingredient |
| --- | --- | --- |
| 10 cups (2.366 L) | 59 | Body Lotion base |
| 5 cups (1.183 L) | 29 | Butternut Squash:Pumpkin extract (70%:30%) containing 1% liquid germall plus (vol %), 1% phenonip (vol %) & 1% potassium benzoate |
| 2½ tablespoons (37 ml) | 0.9 | potassium ascorbate |
| ½ cup (118 ml) | 2.9 | Gel Maker - EMU |
| ½ cup (118 ml) | 2.8 | *Aloe Vera* extract |
| ⅓ cup (78 ml) | 1.9 | Cranberry Seed Oil |
| ⅓ cup (78 ml) | 1.9 | Cyclo-Dimethicone |
| ¼ cup (59 ml) | 1.46 | Honey |
| ½ teaspoon (2.4 ml) | 0.06 | Citric Powder |
| 2 teaspoons (9.9 ml) | 0.2 | Fragrance - scented oil - cucumber melon |
| Total 4049 ml | 100% | |

The butternut squash/pumpkin extract containing 1% germall, 1% phenonip and 1% potassium benzoate was added to the body lotion base and mixed well with a mechanical mixer. Next potassium ascorbate was added and mixed well. Next the gel maker-EMU, aloe vera extract, cranberry seed oil and cyclo-dimethicone were sequentially added and mixed well. Then the honey, citric powder, and scented oil were sequentially added and mixed well. This produced 11-12 oz. (355 ml) bottles.

Results of Using the Body Lotion

Five individuals provided the following reports. "This leaves my skin feeling smooth and soft and also smells amazing!" "Makes my skin feel smooth and also smells great but not overbearing." "I have been using this product for about 6 months and I can really see a difference in the way my skin feels. I also noticed that when I get razor burn on my legs, the lotion soothes the irritation and makes the red bumps go away." "I use it every day, and I love the way it makes my skin feel soft and smooth." "I love it! The scent is great and it leaves a silky shiny look on my skin."

EXAMPLE 13

Face Cream
Formula

A face cream was made in accordance with the formula shown in Table 18.

TABLE 18

| Quantity (by vol.) | Volume % of total | Ingredient |
| --- | --- | --- |
| 4 cups (946 ml) | 39 | Face Cream base |
| 4 cups (946 ml) | 39 | Butternut Squash:Pumpkin extract (70%:30%) containing 1% liquid germall plus (vol %) & 1% potassium benzoate |
| 2 tablespoons (29.6 ml) | 1.2 | potassium ascorbate |
| ½ cup (118 ml) | 4.9 | Honey |
| ½ cup (118 ml) | 4.9 | *Aloe Vera* |

TABLE 18-continued

| Quantity (by vol.) | Volume % of total | Ingredient |
|---|---|---|
| ½ cup (118 ml) | 4.9 | Cranberry Seed Oil |
| ⅓ cup (78.1 ml) | 3.2 | Gel Maker - EMU |
| 2 teaspoons (9.9 ml) | 0.4 | Citric Acid |
| 2 tablespoons (29.6 ml) | 1.23 | Tripeptide 5 |
| 2 teaspoons (9.9 ml) | 0.4 | Fragrance - cucumber melon |
| Total 2405 ml | 100% | |

The butternut squash/pumpkin extract containing 1% germall, 1% phenonip and 1% potassium benzoate was added to the face cream base and mixed well with a mechanical mixer. Next potassium ascorbate was added and mixed well. The honey, Aloe Vera extract, and cranberry seed oil were then sequentially added and mixed. Next the gel maker-EMU, citric acid, tripeptide 5 and fragrance were sequentially added and mixed well. This produced 19-4 oz. (118.3 ml) jars.

Results of Using the Face Cream

Four individuals provided the following reports. "I love putting this on at night and waking up the next morning with soft skin. It doesn't clog my pores either." "No more searching for the right face cream. Not too dry but not too oily, just perfect for every skin type!" "I have semi-oily skin and this cream has worked wonders for me. It leaves my skin feeling soft and smooth." "Makes my skin feel soft and the scent is not too powerful, it's just right."

EXAMPLE 14

Shampoo
Formula

A shampoo was made in accordance with the formula shown in Table 19.

TABLE 19

| Quantity (by vol.) | Volume % of total | Ingredient |
|---|---|---|
| 8 cups (1.892 L) | 55.5 | Shampoo base |
| 4 cups (946.4 ml) | 27.7 | Butternut Squash:Pumpkin extract (70%:30%) containing 1% liquid germall plus (vol %), 1% phenonip (vol %) & 1% potassium benzoate |
| 2 tablespoons (29.6 ml) | 0.9 | potassium ascorbate |
| 1 cup (236 ml) | 6.9 | cocamide betaine |
| ½ cup (118 ml) | 3.5 | *Aloe Vera* extract |
| ½ cup (118 ml) | 3.5 | Honey |
| ¼ cup (59.1 ml) | 1.7 | Glucose-T |
| 2 teaspoons (9.9 ml) | 0.3 | Fragrance pink lemonade |
| Total 3410 ml | 100% | |

The strained butternut squash/pumpkin extract containing 1% germall, 1% phenonip and 1% potassium benzoate was added to the shampoo base and mixed well with a mechanical mixer. Next potassium ascorbate was added and mixed well. The cocamide betaine, Aloe Vera extract, Honey, Glucose-T, and fragrance were then sequentially added and mixed. This produced 8-12 oz. (355 ml) bottles.

Results of Using the Shampoo

Five individuals provided the following individual reports. "This product lathers better than any shampoo I've ever used, and the way it makes my hair feel is phenomenal!" "After using only name brand products for years, I have found that this shampoo has made a tremendous difference in the texture and appearance of my hair." "I love the shampoo and the way it makes my hair feel. I also have a dry scalp and it doesn't make it worse." "I really love the way it makes my hair feel soft and looks fuller with more body." "I have tried very expensive brands of shampoo, and when I started using Early Harvest I noticed it makes my hair just as, if not more, bouncy and smooth to the touch."

EXAMPLE 15

Conditioner
Formula

A conditioner was made in accordance with the formula shown in Table 20.

TABLE 20

| Quantity (by vol.) | Volume % of total | Ingredient |
|---|---|---|
| 8 cups (1.892 L) | 61 | Conditioner base |
| 2 cups (473 ml) | 15 | Butternut Squash:Pumpkin extract (70%:30%) containing 1% liquid germall plus (vol %), 1% phenonip (vol %) & 1% potassium benzoate |
| 1 tablespoon (14.8 ml) | 0.5 | potassium ascorbate |
| 2 cups (473 ml) | 15 | Cyclo-dimethicone |
| ½ cup (118.3 ml) | 3.8 | *Aloe Vera* extract |
| ½ cup (118.3 ml) | 3.8 | grape seed oil |
| ⅛ cup (29.6 ml) | 0.9 | Apple Cider Vinegar |
| 2 teaspoons (9.9 ml) | 0.3 | Fragrance - pink lemonade |
| Total 3128 ml | 100% | |

The strained butternut squash/pumpkin extract containing 1% germall, 1% phenonip and 1% potassium benzoate was added to the conditioner base and mixed well with a mechanical mixer. Next potassium ascorbate was added and mixed well. The Cyclo-dimethicone, Aloe Vera extract, grape seed oil, apple Cider Vinegar and fragrance were then sequentially added and mixed well. This produced 8-12 oz. (355 ml) bottles.

Results of Using the Conditioner

Five individuals provided the following reports. "It didn't make my hair feel heavy or oily like a lot of other conditioners I've used in the past." "The shampoo and conditioner combined have left my hair feeling softer and easier to manage." "This product moisturizes my hair and scalp, leaving it soft and smooth. I also noticed that when I put color on my hair, it often leaves it dry and brittle, but when I use this conditioner it smoothes the follicle down making it easier to brush and style." "The conditioner doesn't make my hair too soft or too flat, like a lot of conditioners can do. It also makes my hair more manageable." "I like it a lot, because it doesn't weigh my hair down or over condition it leaving it oily."

All patents, patent applications, publications, and abstracts cited above are incorporated herein by reference in their entirety. Various embodiments of the invention have been described in fulfillment of the various objectives of the invention. It should be recognized that these embodiments are merely illustrative of the principles of the present invention. Numerous modifications and adaptations thereof will be readily apparent to those of skill in the art without departing from the spirit and scope of the invention. It should be understood that the foregoing relates only to preferred embodiments of the present invention and that numerous modifications or alterations may be made therein without departing from the spirit and the scope of the present invention as defined in the following claims.

What is claimed is:

1. A personal care composition for cleaning and/or moisturizing skin and/or hair comprising a cosmetic base and effective amounts of a preservative and an extract of butternut squash and pumpkin, wherein the preservative comprises phenonip and germall, and wherein the extract is obtained from a combination of butternut squash and pumpkin, wherein the amount of butternut squash in the combination is between about 50%-75% (vol %) and the amount of the pumpkin in the combination is between about 25%-50% (vol %).

2. The personal care composition of claim 1, further comprising a fragrance, an emulsifier, a thickener, or a surfactant, or a combination thereof.

3. The personal care composition of claim 1, wherein the composition contains at least 5%, 10%, 15% or 20% (vol %) of the butternut squash and pumpkin extract.

4. The personal care composition of claim 1, wherein the pumpkin varieties are from species *Cucurbita pepo*, *Cucurbita mixta*, *Cucurbita maxima*, or *Cucurbita moschata*.

5. The personal care composition of claim 1, wherein the personal care composition is a shampoo, conditioner, face cream, hand and body lotion, or body wash.

6. The personal care composition of claim 1, wherein the preservative further comprises DHA, potassium benzoate or a combination thereof.

7. The personal care composition of claim 1, wherein the extract is obtained from the fruit, flesh and seeds of the butternut squash and the pumpkin.

8. The personal care composition of claim 1, wherein the cosmetic base is a base for a shampoo, conditioner, face cream, hand and body lotion, or body wash.

9. The personal care composition of claim 1, wherein the amount of butternut squash in the combination is about 50% and the amount of the pumpkin in the combination is about 50%; wherein the amount of butternut squash in the combination is about 75% and the amount of the pumpkin in the combination is about 25%, wherein the amount of butternut squash in the combination is about 70% and the amount of the pumpkin in the combination is about 30%, or wherein the amount of butternut squash in the combination is about 60% and the amount of the pumpkin in the combination is about 40%.

10. The personal care composition of claim 1, wherein the composition comprises 1% phenonip and 1% germall by volume of the butternut squash and pumpkin extract.

11. The personal care composition of claim 1, wherein the composition comprises between about 10%-50% of the butternut squash and pumpkin extract.

12. A personal care composition for cleaning and/or moisturizing skin and/or hair comprising, a cosmetic base and effective amounts of an extract of butternut squash and pumpkin and a preservative, wherein the preservative is obtained from phenopin and germall, and wherein the extract is obtained from a combination of butternut squash and pumpkin, wherein the amount of butternut squash in the combination is between about 50%-75% (vol %) and the amount of the pumpkin in the combination is between about 25%-50% (vol %), wherein the personal care composition is a shampoo, conditioner, face cream, hand and body lotion, or body wash, wherein the cosmetic base is a base for the shampoo, conditioner, face cream, hand and body lotion, or body wash, and wherein the extract is obtained from the fruit, flesh and seeds of the butternut squash and the pumpkin.

13. The personal care composition of claim 12, wherein the amount of butternut squash in the combination is about 50% and the amount of the pumpkin in the extract is about 50%; wherein the amount of butternut squash in the combination is about 75% and the amount of the pumpkin in the combination is about 25%, wherein the amount of butternut squash in the combination is about 70% and the amount of the pumpkin in the combination is about 30% or wherein the amount of butternut squash in the combination is about 60% and the amount of the pumpkin in the combination is about 40%.

14. The personal care composition of claim 12, wherein the composition comprises 1% phenonip and 1% germall by volume of the butternut squash and pumpkin extract.

15. The personal care composition of claim 12, wherein the composition comprises between about 10%-50% of the butternut squash and pumpkin extract.

16. An extract of butternut squash and pumpkin, wherein the extract is made by a method comprising:
   obtaining a combination of butternut squash and the pumpkin, wherein the amount of butternut squash in the combination is between about 50%-75% (vol %) and the amount of the pumpkin in the combination is between about 25%-50% (vol %);
   removing the stem from the butternut squash and from the pumpkin;
   dicing the butternut squash and the pumpkin to obtain fragments;
   juicing the butternut squash and the pumpkin fragments to obtain a liquid;
   straining the liquid to obtain the butternut squash and pumpkin extract; and,
   adding an effective amount of a preservative to the butternut squash and pumpkin extract, wherein the preservative comprises phenonip and germall.

17. The extract of claim 16, wherein the preservative further comprises DHA, potassium benzoate or a combination thereof.

18. The extract of claim 16, wherein the extract is obtained from the fruit, flesh and seeds of the butternut squash and the pumpkin.

19. A method of making a personal care composition for cleaning and/or moisturizing skin and/or hair comprising a cosmetic base and an extract of butternut squash and pumpkin comprising:
   obtaining a combination of butternut squash and pumpkin, wherein the amount of butternut squash in the combination is between about 50%-75% (vol %) and the amount of the pumpkin in the combination is between about 25%-50% (vol %);
   removing the stem from the butternut squash and from the pumpkin
   dicing the butternut squash and the pumpkin to obtain fragments;
   juicing the butternut squash and the pumpkin fragments to obtain a liquid;
   straining the liquid to obtain the butternut squash and pumpkin extract,
   adding an effective amount of a preservative to the butternut squash and pumpkin extract, wherein the preservative comprises phenonip and germall; and,
   mixing the extract and the cosmetic base.

20. The method of claim 19, wherein in step (f) one or more emulsifier(s) and fragrance(s) are added to the butternut squash and pumpkin extract and mixed before addition of the cosmetic base.

21. The method of claim 19, wherein the preservative further comprises DHA, potassium benzoate or a combination thereof.

22. The method of claim 19, wherein about 1% phenonip and about 1% germall by volume are added to the butternut squash and pumpkin extract.

23. A personal care composition made according to the method of claim 19, wherein the composition contains at least 5%, 10%, 15% or 20% (vol %) of the butternut squash and pumpkin extract.

24. A personal care composition made according to the method of claim 19.

25. The personal care composition of claim 24, wherein the personal care composition is a shampoo, conditioner, face cream, hand and body lotion, or body wash.

26. A method of cleaning and moisturizing hair and/or skin, comprising applying to said hair and/or skin an effective amount of the personal care composition according to claim 1.

\* \* \* \* \*